US009518902B2

(12) United States Patent
Chen et al.

(10) Patent No.: US 9,518,902 B2
(45) Date of Patent: Dec. 13, 2016

(54) EMBEDDER

(71) Applicant: Leica Microsystems Ltd. Shanghai, Shanghai (CN)

(72) Inventors: Ningjiang Chen, Shanghai (CN); Yuan Chu, Shanghai (CN); Chonglu Wang, Shanghai (CN)

(73) Assignee: Leica Microsystems Ltd. Shanghai, Shanghai (CN)

( * ) Notice: Subject to any disclaimer, the term of this patent is extended or adjusted under 35 U.S.C. 154(b) by 0 days.

(21) Appl. No.: 14/953,318

(22) Filed: Nov. 28, 2015

(65) Prior Publication Data

US 2016/0187238 A1  Jun. 30, 2016

(30) Foreign Application Priority Data

Dec. 29, 2014 (CN) .................... 2014 2 0865327 U

(51) Int. Cl.
*A61B 10/00* (2006.01)
*G01N 1/36* (2006.01)

(52) U.S. Cl.
CPC ...................................... *G01N 1/36* (2013.01)

(58) Field of Classification Search
CPC .................................. C12M 1/00; G01N 1/36
See application file for complete search history.

(56) References Cited

U.S. PATENT DOCUMENTS 6,440,725 B1 * 8/2002 Pourahmadi ...... B01L 3/502715
422/547
2011/0076753 A1 * 3/2011 Goerner .................. G01N 1/36
435/283.1

FOREIGN PATENT DOCUMENTS

EP        1627938      2/2006
EP        2104655      9/2009

* cited by examiner

*Primary Examiner* — Jyoti Nagpaul
(74) *Attorney, Agent, or Firm* — Hodgson Russ LLP

(57) ABSTRACT

An embedder is provided. The embedder includes a body having a working stand; a paraffin reservoir disposed in the body; a paraffin dispenser disposed on the body and connected with the paraffin reservoir; a heated working plate disposed on the working stand; a cooling plate disposed on the working stand; a tray disposed on the working stand; and a ceramic layer at least formed on an inner wall surface of the tray. With the embedder according to the present invention, by coating the ceramic layer on the inner wall surface of the tray to form an anti-scratch protective layer, when removing solidified paraffin wax on the inner wall surface of the tray, it is possible to avoid scratching the inner wall surface of the tray so as to avoid the damage to the surface of the tray.

8 Claims, 2 Drawing Sheets

EMBEDDER

CROSS REFERENCE TO RELATED APPLICATIONS

This application claims priority of Chinese application number 201420865327.0 filed Dec. 29, 2014, the entire disclosure of which is incorporated by reference herein.

FIELD OF THE INVENTION

The present invention relates to a device for embedding specimens in paraffin wax, and more particularly to an embedder.

BACKGROUND OF THE INVENTION

An embedder is a device for embedding specimens in paraffin wax. The specimens are arranged in mold having openings, and liquid paraffin wax is poured into the mold and then cooled to solidify, so as to embed the specimens. The embedder generally includes a heated working plate and a cooling plate. The working plate has grooves through which runoff of overflowing paraffin wax flows. The cooling plate is used to cool paraffin wax embedding specimens. The embedder in the related art is inconvenient to use, and solidified paraffin wax is hard to clean.

SUMMARY OF THE INVENTION

The present invention is proposed based on the following facts and problems found and recognized by the inventors.

With the embedder in the related art, the paraffin wax may be solidified on the surface of the grooves, the working plate, the cooling plate or the paraffin reservoir. When removing the solidified paraffin wax by means of an instrument, it tends to scratch the surface of the working plate, the cooling plate, or the paraffin reservoir. In addition, the embedder in the related art does not have a space for disposing cassettes, molds and other operating instruments, such that the embedder is inconvenient to use.

The present invention seeks to solve at least one of the problems existing in the related art to at least some extent. Accordingly, the present invention provides an embedder, which is convenient to use and with which solidified paraffin wax is easy to clean.

The embedder according to an embodiment of the present invention includes a body having a working stand; a paraffin reservoir disposed in the body; a paraffin dispenser disposed on the body and connected with the paraffin reservoir; a heated working plate disposed on the working stand; a cooling plate disposed on the working stand; a tray disposed on the working stand; and a ceramic layer at least formed on an inner wall surface of the tray.

With the embedder according the present invention, by providing the tray on the working stand, the cassette and/or the mold may be conveniently placed in the tray, such that the embedder is convenient to use. Moreover, by forming the ceramic layer on the inner wall surface of the tray to form an anti-scratch protective layer, when removing solid paraffin wax solidified on the inner wall surface of the tray, it is possible to avoid scratching the inner wall surface of the tray so as to avoid the damage to the surface of the tray.

Preferably, the tray has a tray lid thereon, and the ceramic layer is further formed on an inner wall surface of the tray lid.

Preferably, the ceramic layer is further formed on surfaces of the heated working plate and the cooling plate.

Preferably, the ceramic layer is further formed on an inner wall surface of the paraffin reservoir and an inner wall surface of a dispensing outlet of the paraffin dispenser.

Preferably, a forcep holder is disposed on the working stand, and the ceramic layer is further formed on a surface of the forcep holder.

Preferably, the ceramic layer is a zirconia ceramic layer.

Preferably, a groove is formed in a surface of the working stand, and the tray is disposed within the groove.

Preferably, two trays are provided and spaced apart from each other in a left and right direction, and the heated working plate and the cooling plate are located in front of the trays.

Preferably, a dispensing outlet of the paraffin dispenser is located above the heated working plate.

Preferably, a paraffin collection container is disposed in the working stand, the paraffin collection container is able to be pulled out of or pushed into the working stand, the heated working plate has a guide channel for runoff of overflowing paraffin wax, and the heated working plate has a plurality of holes in the guide channel for paraffin wax to flow through to the paraffin collection container.

BRIEF DESCRIPTION OF THE DRAWING VIEWS

REFERENCE NUMERALS

| | |
|---|---|
| 1 | embedder |
| 11 | body |
| 111 | working stand |
| 12 | paraffin reservoir |
| 13 | paraffin dispenser |
| 14 | heated working plate |
| 141 | guide channel |
| 142 | notch |
| 15 | cooling plate |
| 16 | tray |
| 161 | tray lid |
| 17 | ceramic layer |
| 18 | forcep holder |
| 19 | paraffin collection container |

DETAILED DESCRIPTION OF THE INVENTION

Reference will be made in detail to embodiments of the present invention. The embodiments described herein with reference to drawings are explanatory, illustrative, and used to generally understand the present invention. The embodiments shall not be construed to limit the present invention.

Figure 1:
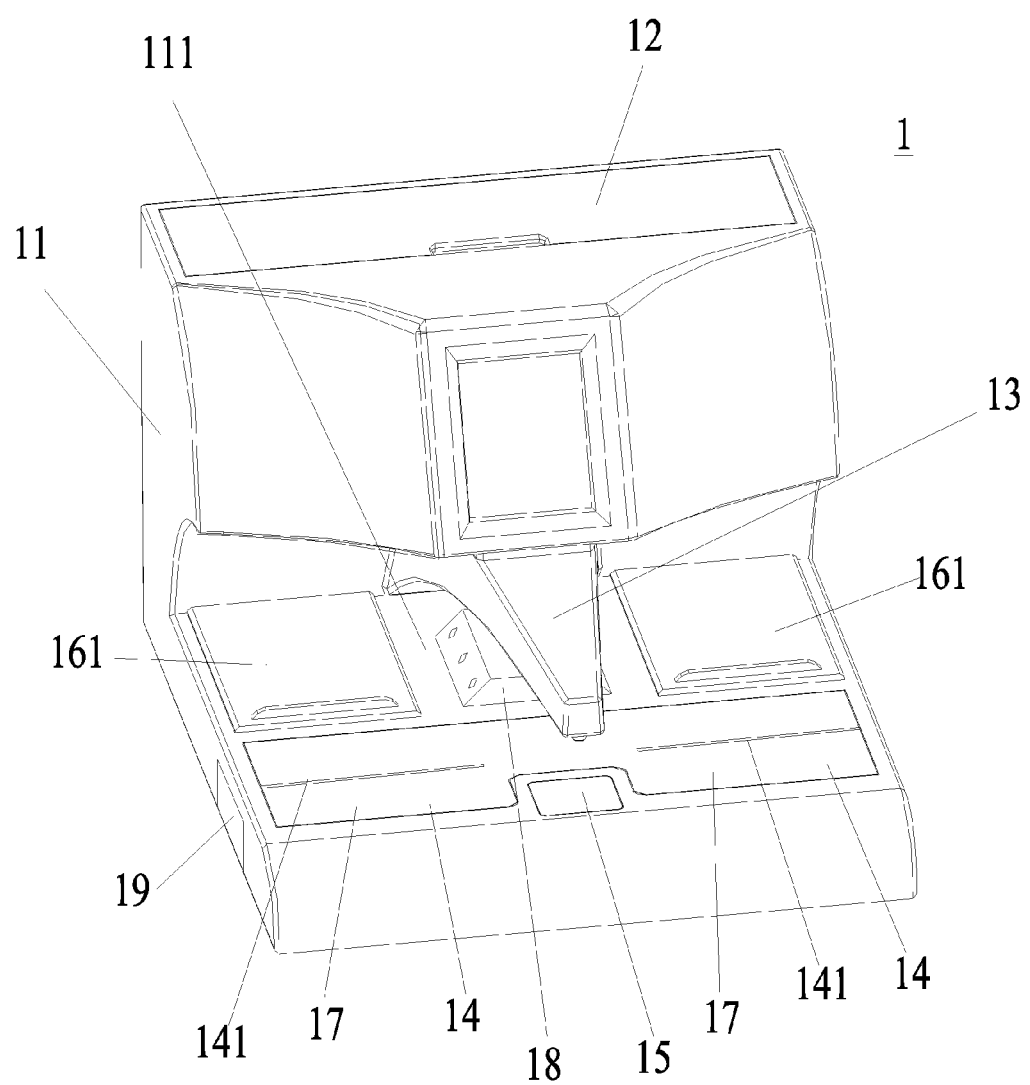
FIG. 1 is a schematic view of an embedder according to an embodiment of the present invention.
Figure 2:
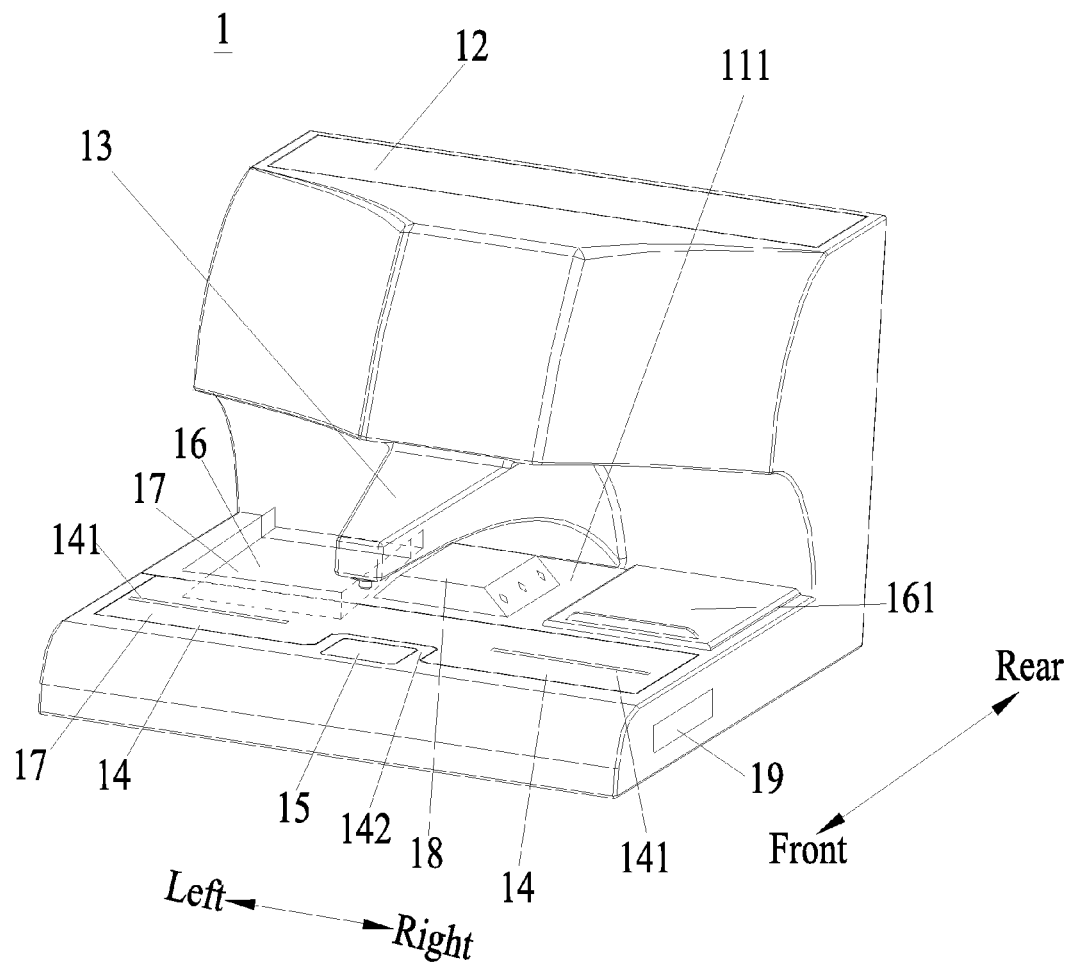
FIG. 2 is a schematic perspective view of an embedder according to an embodiment of the present invention.

As shown in FIGS. 1-2, an embedder 1 according to an embodiment of the present invention includes a body 11, a paraffin reservoir 12, a paraffin dispenser 13, a heated working plate 14, a cooling plate 15, a tray 16, and a ceramic layer 17.

The body 11 has a working stand 111. The paraffin reservoir 12 is disposed in the body 11 for containing molten liquid paraffin wax. For example, the paraffin reservoir 12 may be a chamber formed in the upper part of the body 11.

The paraffin dispenser 13 is disposed on the body 11 and connected with the paraffin reservoir 12. The liquid paraffin wax flows into the paraffin dispenser 13 from the paraffin reservoir 12 so as to be dispensed into the mold containing specimens therein from a dispensing outlet of the paraffin dispenser 13. Preferably, the dispensing outlet of the paraffin dispenser 13 is located above the heated working plate 14.

The cooling plate 15 and the heated working plate 14 are disposed on the working stand 111 respectively. The heated working plate 14 is used to support the mold containing the specimens therein. A paraffin collection container 19 is disposed in the working stand 111 for collecting overflowing paraffin wax. Preferably, the heated working plate 14 is formed with a plurality of guide channels 141 for runoff of the paraffin wax overflowing on the heated working plate 14. The heated working plate 14 has a plurality of holes in the guide channels 141 through which the overflowing paraffin wax flows into the paraffin collection container 19. The paraffin collection container 19 is configured like a drawer, which can be pushed into or pulled out of the working stand 14.

The tray 16 is disposed on the working stand 111 for receiving cassettes and/or molds. For example, when the embedder 1 operates, the tray 16 contains molten liquid paraffin wax, and the cassettes and/or the molds are placed in the liquid paraffin wax. Preferably, the working stand 111 is formed with a groove, and the tray 16 is disposed in the groove, so that the upper edge of the tray 16 is flush with the upper surface of the working stand 111. Each of the heated working plate 14, the cooling plate 15 and the tray 16 may be made of a metal, such as aluminum or stainless steel.

The ceramic layer 17 is formed or coated on an inner wall surface of the tray 16. In other words, the ceramic layer 17 is coated on a bottom wall and a peripheral wall of the tray 16. Preferably, the ceramic layer 17 may be a zirconia ceramic layer.

With the embedder according to embodiments of the present invention, by providing the tray on the working stand, the cassettes and/or the molds may be conveniently placed in the tray, such that the embedder is convenient to use. Moreover, by forming the ceramic layer on the inner wall surface of the tray to form an anti-scratch protective layer, when removing solidified paraffin wax on the inner wall surface of the tray, it is possible to avoid scratching the inner wall surface of the tray so as to avoid the damage to the surface of the tray.

As shown in FIG. 2, in some embodiments, the tray 16 is provided with a tray lid 161 thereon. Two trays 16 may be provided and spaced apart from each other in a left and right direction. For example, the cassettes and the molds may be placed in different trays 16 respectively. The heated working plate 14 and the cooling plate 15 are located in front of the trays 16. As shown in FIG. 2, a notch 142 recessed backwardly is formed in a middle of the heated working plate 14, and at least a part of the cooling plate 15 is located in the notch 142.

The working stand 111 is further provided with a forcep holder 18 thereon. The forcep holder 18 may be disposed between the two trays 16, and forceps for clamping the cassette and/or specimens may be placed on the forcep holder 18, such that the forceps are convenient to use.

In some embodiments, the ceramic layer 17 may also be coated on at least one of a surface of the heated working plate 14, a surface of the cooling plate 15, an inner wall surface of the tray lid 161, a surface of the forcep holder 18, an inner wall surface of the paraffin reservoir 12, an inner wall surface of a dispensing outlet of the paraffin dispenser 13. Preferably, the ceramic layer 17 is coated on all the above surfaces. Since paraffin wax is likely to solidify on the above surfaces, by coating the ceramic layer 17 on the above surfaces, when removing paraffin wax from these surfaces, it is possible to avoid scratching these surfaces so as to avoid the damage to these surfaces. Moreover, the paraffin wax solidified on the above surfaces is easily separated from the ceramic layer 17, so that it is convenient to clean.

The operation of the embedder according to embodiments of the present invention will be simply described below.

When the specimen is needed to be embedded, the cassette is taken out of the tray 16 using forceps placed on the forcep holder 18, and a cassette cover is removed from a cassette body to open the cassette. Then, the mold with a suitable size is selected and placed on the heated working plate 14 below the dispensing outlet of the paraffin dispenser 13, and liquid paraffin wax in the paraffin reservoir is dispensed into the mold, preferably the filling volume of the paraffin wax into the mold is ¼ of a capacity of the mold. Next, the specimen is placed in the paraffin wax contained in the mold using forceps, and then the cassette body is placed on a top of the mold. Next, the mold is placed on the heated working plate 14 below the dispensing outlet of the paraffin dispenser 13 again, so that the liquid paraffin wax in the paraffin reservoir is filled into the mold containing the cassette body and the specimen. After that, the mold is moved onto the cooling plate 15 for cooling the liquid paraffin wax, after the liquid paraffin wax is solidified to be a paraffin wax block, the paraffin wax block containing the specimen and the cassette body fixed with the paraffin wax block are taken out of the mold. Finally, the paraffin wax block is trimmed excess paraffin wax from all edges of the cassette body, and the operation of the embedder according to the present invention is accomplished.

The paraffin wax overflowing onto the heated working plate 14 flows into the paraffin collection container 19 via the guide channel 141 and the holes in the guide channel 141. When the solidified paraffin wax on the embedder needs to be cleaned, for example, the solidified paraffin wax in the tray 16 needs to be cleaned, the solidified paraffin wax may be scraped off by means of an instrument. Since the inner wall surface of the tray 16 is formed with the ceramic layer 17, the surface of the tray 16 will not be scratched, thus increasing the life of the tray, and the paraffin wax is convenient to clean.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present invention, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present invention. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present invention. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present invention, and changes, alternatives, and modifications can be made in the embodiments without departing from spirit, principles and scope of the present invention.

What is claimed is:

1. An embedder, comprising:
   a body having a working stand;
   a paraffin reservoir disposed in the body;
   a paraffin dispenser disposed on the body and connected with the paraffin reservoir;
   a heated working plate disposed on the working stand;
   a cooling plate disposed on the working stand;
   a tray disposed on the working stand; and
   a ceramic layer at least formed on an inner wall surface of the tray, an inner wall surface of the paraffin reservoir, and an inner wall surface of a dispensing outlet of the paraffin dispenser, wherein the ceramic layer is a zirconia ceramic layer.

2. The embedder according to claim 1, wherein the tray has a tray lid thereon, and the ceramic layer is further formed on an inner wall surface of the tray lid.

3. The embedder according to claim 1, wherein the ceramic layer is further formed on surfaces of the heated working plate and the cooling plate.

4. The embedder according to claim 1, wherein a forcep holder is disposed on the working stand, and the ceramic layer is further formed on a surface of the forcep holder.

5. The embedder according to claim 1, wherein a groove is formed in a surface of the working stand, and the tray is disposed within the groove.

6. The embedder according to claim 5, wherein two trays are provided and spaced apart from each other in a left and right direction, and the heated working plate and the cooling plate are located in front of the two trays.

7. The embedder according to claim 1, wherein a dispensing outlet of the paraffin dispenser is located above the heated working plate.

8. The embedder according to claim 1, wherein a paraffin collection container is disposed in the working stand, the paraffin collection container is able to be pulled out of or pushed into the working stand, the heated working plate has a guide channel for runoff of overflowing paraffin wax, and the heated working plate has a plurality of holes in the guide channel for paraffin wax to flow through to the paraffin collection container.

* * * * *